US00RE38879E

(19) United States
(12) Reissued Patent
Goodman et al.

(10) Patent Number: US RE38,879 E
(45) **Date of Reissued Patent: *Nov. 15, 2005**

(54) EXTRAVASATION DETECTION TECHNIQUE

(75) Inventors: Jack Goodman, Ann Arbor, MI (US); Arthur Zimmet, Centerport, NY (US)

(73) Assignee: E-Z-EM, Inc., Lake Success, NY (US)

( * ) Notice: This patent is subject to a terminal disclaimer.

(21) Appl. No.: 09/948,277

(22) Filed: Sep. 7, 2001

Related U.S. Patent Documents

Reissue of:
(64) Patent No.: 5,947,910
Issued: Sep. 7, 1999
Appl. No.: 08/980,094
Filed: Nov. 26, 1997

U.S. Applications:
(63) Continuation-in-part of application No. 08/957,121, filed on Oct. 24, 1997, now Pat. No. 5,964,703, which is a continuation-in-part of application No. 08/924,631, filed on Sep. 5, 1997, now abandoned, which is a continuation of application No. 08/491,149, filed on Jun. 16, 1995, now abandoned, which is a continuation of application No. 08/323,595, filed on Oct. 17, 1994, now abandoned, which is a continuation-in-part of application No. 08/182,221, filed on Jan. 14, 1994, now abandoned.

(51) Int. Cl.[7] ..... A61B 5/05
(52) U.S. Cl. ..... 600/547; 600/382; 600/384; 600/393; 600/396; 604/66; 604/503; 604/506
(58) Field of Search ..... 600/547, 372, 600/382, 384, 386, 393, 396, 506; 604/503, 506, 507, 508, 65–67, 245; 340/573; 128/DIG. 13

(56) References Cited

U.S. PATENT DOCUMENTS

| | | | | |
|---|---|---|---|---|
| 3,779,079 | A | 12/1973 | Snook | 73/346 |
| 4,010,749 | A | 3/1977 | Shaw | 128/214 |
| 4,378,808 | A | 4/1983 | Lichtenstein | 128/736 |
| 4,534,756 | A | 8/1985 | Nelson | 604/50 |
| 4,572,182 | A | 2/1986 | Royse | 128/325 |
| 4,647,281 | A | 3/1987 | Carr | 604/50 |
| 4,648,869 | A | 3/1987 | Bobo, Jr. | 604/49 |
| 4,653,501 | A | 3/1987 | Cartmell et al. | 128/640 |
| 4,667,679 | A | 5/1987 | Sahota | 128/663 |
| 4,729,385 | A | 3/1988 | Juncosa et al. | 128/734 |
| 4,743,228 | A | 5/1988 | Butterfield | 604/50 |
| 4,816,019 | A | 3/1989 | Kamen | 604/65 |
| 4,877,034 | A | 10/1989 | Atkins et al. | 128/664 |
| 4,898,576 | A | 2/1990 | Philip | 604/50 |
| 4,959,050 | A | 9/1990 | Bobo, Jr. | 604/49 |
| 5,026,348 | A | 6/1991 | Venegas | 604/122 |
| 5,246,008 | A | 9/1993 | Mueller | 128/698 |
| 5,334,141 | A | 8/1994 | Carr et al. | 604/50 |
| 5,353,802 | A | 10/1994 | Ollmar | 128/734 |
| 6,408,204 | B1 | 6/2002 | Hirschman | 600/547 |
| 6,459,931 | B1 | 10/2002 | Hirschman | 600/547 |

FOREIGN PATENT DOCUMENTS

| | | |
|---|---|---|
| EP | 784960 A1 | 7/1997 |
| SU | 757151 | 9/1980 |
| WO | WO99/29356 | 6/1999 |

OTHER PUBLICATIONS

Contrast Media—Early Detection of Extravasation of Radiographic Contrast Medium, James Shaeffer, PhD, Sture V. Sigfred, MD, Matthew A. Sevcik, MD, Richard S. Grabowy, MS, Lee Ann Gemmell, BSEE, Alan D. Hirschman, PhD; Jul. 1992.

(Continued)

*Primary Examiner*—Ruth S. Smith
(74) *Attorney, Agent, or Firm*—Alston & Bird LLP

(57) ABSTRACT

The technique for detecting extravasation during the injection of fluid into a patient involves the establishment of a baseline representing impedance at the zone of the injection prior to the injection starting. Extravasation is signaled when at least two characteristics appear. First is that the impedance varies from the baseline more than a predetermined amount in more than a predetermined number of discreet time slots called epochs herein. Second is that, the rate of change of the impedance, which is called the slope herein, is consistently greater than a predetermined amount.

45 Claims, 4 Drawing Sheets

OTHER PUBLICATIONS

Cancer letters—Detection of Extravasation of Antineoplastic Drugs by Microwave Radiometry, James Shaeffer, Anas M. El–mahdi, Albert E. Hamwey Jr., and Kenneth L. Carr; Apr. 1, 1986.

MMIC Receiver for Water–Vapor Radiometer, NASA Tech Briefs, Sep. 1993.

Recent Development in Modeling Heat Transfer in Blood Perfused Tissues, H. Arkin, L. Xi Xu and K. R. Holmes, IEEE Transactions on Biopmedical Enginnering vol. 41, No. 2, Feb. 1994.

Infusion Line Model for the Detection of Infiltration Extravasation, and other Fluid Flow Faults, Thomas S. Harris and Wolf W. von Maltzahn, Senior Member IEEE, IEEE Transaction on Biomedical Engineering vol. 40, No. 2 Feb. 1993.

Multiangle Method for Temperature Measurement of Biological Tissues by Microwave Radiometry, Jean Montreuil and Manfred Nachman, Transactions on Microwave Theory and Techniques vol. 39 No. 7, Jul. 1991.

Use of Gallium Arsenide in Medical Applications by Ken Carr ©1995.

EXTRAVASATION DETECTION TECHNIQUE

Matter enclosed in heavy brackets [ ] appears in the original patent but forms no part of this reissue specification; matter printed in italics indicates the additions made by reissue.

REFERENCE TO RELATED APPLICATIONS

This application is a continuation-in-part of application Ser. No. 08/957,121 filed on Oct. 24, 1997 titled: Extravasation Detection, *now U.S. Pat. No. 5,964,703* which is a continuation-in-part of application Ser. No. 08/924,631 filed Sep. 5, 1997, now abandoned, which is a continuation of application Ser. No. 08/491,149 filed on Jun. 16, 1995, now abandoned, which in turn is a continuation of application Ser. No. 08/323,595 filed on Oct. 17, 1994, now abandoned, which in turn is a continuation-in-part of application Ser. No. 08/182,221 filed on Jan. 14, 1994 now abandoned; all of which are titled: Extravasation Detection System.

Further details of the patch which is employed in a preferred embodiment of this invention are disclosed in said application filed on Oct. 24, 1997 entitled: Extravasation Detection *now U.S. Pat. No. 5,964,703*. The contents of said [Oct. 24, 1997 application] *U.S. Pat. No. 5,964,703* is incorporated herein by reference.

BACKGROUND OF THE INVENTION

This invention relates to a device and method for the detection of extravasation and more particularly to the detection of extravasation of ionic and non-ionic contrast media.

Extravasation or infiltration is a complication related to the use of power injectors during contrast fluid media injection procedures. When an extravasation occurs, contrast is injected into the tissue surrounding the blood vessel, instead of into the blood vessel itself. The causes for extravasation vary, ranging from operator error in placement of the needle to physiological limitations of the blood vessel to tolerate the rate of fluid administration.

Complications related to extravasation may be quite severe and may include tissue necrosis. This may require reconstructive surgery to repair.

Presently, the only method for detecting an extravasation is for the operator to visually observe it. However, by the time an extravasation is visually observable, much of the previously discussed damage may have occurred.

Accordingly, it is an object of the present invention to provide a safe, efficient, inexpensive and reliable means for the early detection of extravasations.

A very large number of contrast media injection procedures are undertaken each year in the United States; something in the order of ten million. Less than 0.2% of these procedures result in an extravasation. Yet the absolute number is substantial because the base number is so large. The occurrence of an extravasation requires that the procedure be terminated and reinstituted. Accordingly, in a normal situation where an extravasation occurs, early detection is important from the point of view of minimizing the impact on the patient, saving time and providing a timely reinstitution of the procedure.

Although extravasation is not life-threatening, when it does occur it causes discomfort to the patient. It requires a great deal of attention from the doctor and usually means that a procedure has to be interrupted. Thus, it is important that any extravasation detection technique avoid a false indication of extravasation.

In relatively rare cases the extravasation can be quite harmful to the patient. Therefore early detection will avoid patient trauma or other injury.

The false detection of an extravasation results in terminating a procedure. Starting the procedure constitutes unnecesary trauma to the patient and expense. Therefore, any detection technique that gives a noticeable number of false indications will not be used by the doctor.

Accordingly, it is important that any detection technique to be acceptable combine an extremely small number of false indications of extravasation coupled with a reasonably high specificity to the extravasation event being detected.

The relatively large number of contrast media injections undertaken coupled with the relatively small percentage of extravasations that occur means that any procedure to be acceptable to the medical profession has to be non-invasive.

It is an accepted fact that any invasive procedure carries with it risks and trauma. They are to be avoided unless the benefit trade-off warrants such.

In order for an extravasation detection technique to be acceptable in this context, it must provide next to no false indications of extravasation. A false indication would mean stopping a procedure which did not have to be stropped. Thus the technique must be specific to extravasation and non-responsive to other phenomenon such as the patient moving his or her arm.

BRIEF DESCRIPTION

Figure 1:
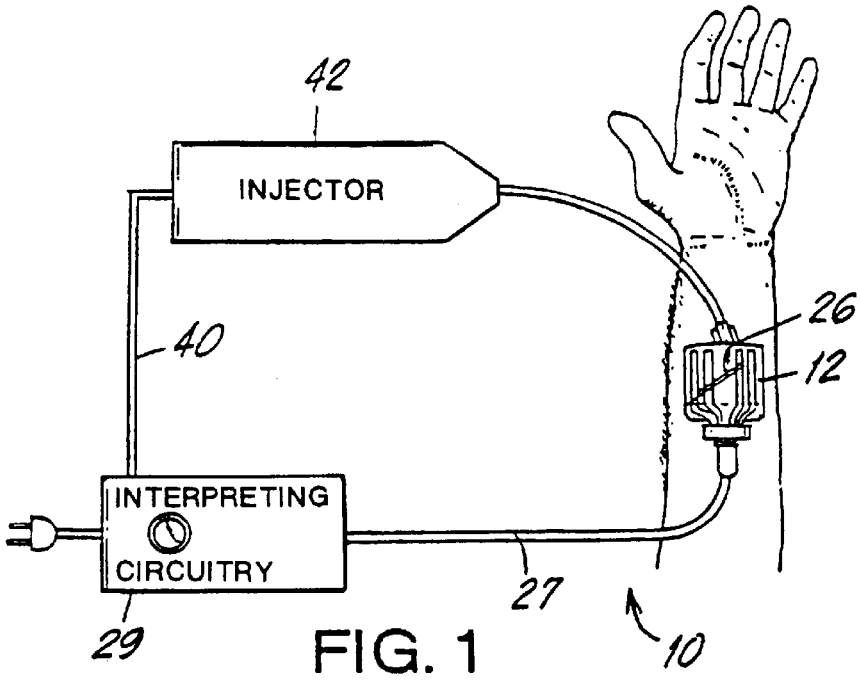
FIG. 1 is a diagrammatic view of a system employing the processing of this invention.

In brief, this invention involves a technique of detecting extravasation that may occur when a needle is inserted into a patient for the purpose of delivering fluid into the patient's vascular system.

At the site of the injection, a patch is applied having excitation electrodes and pick -up electrodes. A high frequency signal applied by the excitation electrodes is coupled to the pick-up electrodes through the patient's body under the patch. The value of the signal picked up by the pick-up electrodes is a function of the body impedance at the site.

A baseline impedance is determined prior to the start of injection. When fluid is injected into the vascular system, no significant change in the pick-up signal occurs. However, if there is an extravasation, the pool of fluid that collects at the site will materially change the impedance value detected.

Accordingly, a baseline impedance is established prior to the injection to represent the impedance condition at the site. Deviations from that baseline condition, if they exceed certain thresholds, are deemed to indicate an extravasation.

In the procedure involved, there are certain stages or states, prior to the injection, which are used to determine that there is sufficient stability in the impedance at the site and to determine the baseline. After these pre-injection states have determined the baseline impedance and the injection is to proceed, a Run State is initiated in which measurements of impedance value changes and rate of change (that is, slope) are determined. If during this Run State, the values of the changes in impedance, and most importantly, the values of the impedance slope are greater than certain thresholds, an indication of extravasation is given to the operator and the injection procedure can be stopped.

In order to minimize the occurrence of false-positives (false indications of extravasation), certain constraints are established on the response to the changes in impedance values from the initial baseline. One constraint is that a predetermined number of measurements have to be made that deviate past a certain threshold from the baseline. Another important requirement is that the rate of change of the impedance measurements has to exceed a certain absolute value and it has to do so on a consistent basis. During this Run State check, if certain relatively low value impedance measurements are made and certain relatively low slope measurements are made, the Run procedure resets either entirely or in part. These reset occasions are to minimize the occurrence of false-positives.

Definitions.

Certain terms used in this application have meanings which may not be evident from the literature. Other terms are best understood before reading the detailed description. The following terms are used with the following definitions. An understanding of the disclosure, as well as the scope of the claims, requires an understanding of these definitions.

Point. One hundred impedance measurements are taken every second. Each measurement is called a point. The impedance measurement is based on the amplitude of an a.c. signal induced in a pick up coil coupled to the zone on the patient where an extravasation would be manifest. An analog to digital converter provides a digital value for the impedance for analysis in an appropriately programmed microprocessor.

Epoch. An epoch is the term for a pre-determined time period. In the embodiment described, this time period is 0.2 seconds. The epoch time can be varied depending on the particular application involved and the sensitivity required. During each epoch, a number of point measurements are taken. In the embodiment described, up to twenty points are taken during each epoch.

Filter Envelope. This is an envelope used for the filtering of spikes. It is equal to plus and minus four (±4) ohms around the epoch impedance average that is calculated at the point involved.

Valid Point. A point within the filter envelope is a valid point. However, a point that is outside the filter envelope but is less than or equal to five ohms from the prior point is also a valid point.

Accepted Epoch. This is an epoch that contains eighty percent or more valid points out of the twenty points calculated during each epoch in this embodiment.

Rejected Epoch. This is an epoch that contains less than eighty percent valid points.

Base Epsilon Criteria. The base epsilon criteria is two ohms. The current epoch impedance is compared to the epoch impedance average up to that point. If the current epoch is an accepted epoch and is within the two ohm base epsilon criteria, it is deemed a good epoch. It the accepted epoch fails the base epsilon criteria, it is deemed a bad epoch.

Range. An impedance range of 40 ohms to 225 ohms has been selected to represent the range within which meaningful impedance measurements might occur. If at any time, an epoch average is outside this range, the process starts over; that is, the system resets to the Initial State.

Epoch Impedance. An impedance value is assigned to each epoch. This impedance value is based on the average of the up to twenty valid point measurements taken during each epoch. It should be noted that there is a requirement that a point be within a certain range so that if a few points are aberrational they will not be used to calculate the epoch impedance. That is, spikes are eliminated. Except for certain rejected epochs, there is an impedance value assigned to each epoch. That impedance value, although an average of a number of points, is a single value and is the basis for most of the calculations involved in this process.

Sliding Window. The epoch impedance average and epoch impedance slopes defined below are based on a plurality of epochs. Up to seventy five epochs constitute the window for determining epoch impedance average. Seven epochs are the window used for calculating epoch impedance slope values. As the latest epoch occurs, the earliest of the epochs in the window is dropped and the latest epoch included. This moving window is called a sliding window. Thus successive value calculations are based on similar sets of epochs, one epoch at a time being replaced. Thus the successive average impedance values and slope values do not change a great deal. The values are keyed to the most recent epoch in the window. But that is essentially an arbitrary matter. The point is there is a sliding window which in particular is one that is quantized in that it increments by one epoch each time it "slides".

Epoch Impedance Average (Also: Epoch Impedance Sliding Window Average). An epoch impedance average is an averaging of the point impedances of a plurality of consecutive epochs. This is distinct from the averaging of the up to twenty points which provide an epoch impedance. This epoch impedance average is based on a sliding window of epochs. Thus it is also called an Epoch Impedance Sliding Window Average. In the embodiment disclosed, it is the average of points in up to seventy-five epochs including the epoch under consideration. Thus as each epoch progresses, the sliding window drops the earliest epoch involved and adds the new epoch. Under initial conditions, this epoch impedance average will encompass less than 75 epochs. The epoch impedance average is used to provide the baseline for the Run State and in calculation of the base epsilon criteria.

The calculation of epoch impedance average is based on the valid points in the window rather than an average of the epoch impedances. In the up to seventy five epoch window, all valid points, except points in rejected epochs, are used and those points are averaged. Thus valid points in bad epochs are employed as well as valid points in good epochs. But when a rejected epoch is within the seventy-five epoch window, all of the points, including valid points, are ignored for the purpose of calculating epoch impedance average.

Good Epoch. A good epoch is an epoch in the pre-injection stages which meets certain criteria that essentially are (a) it has 80% of its points within a range that filters out spikes and (b) it has an epoch impedance that is within two ohms of whatever epoch impedance average is calculated at that point in processing. This means that a good epoch has at least 80% valid points and passes the base epsilon test.

Bad Epoch. A bad epoch is an epoch in the pre-injection stages which, like the good epoch, has 80% of its points within the range that filters out spikes and thus is an accepted epoch. But a bad epoch fails the base epsilon test.

Run State. There are various processing stages prior to the start of fluid injection into a patient. The Run State is the stage of extravasation checking which starts at the start of fluid injection.

Baseline. The baseline is the epoch impedance sliding window average established just prior to the start of the Run State. It is used as the basis for detecting impedance deviations that may indicate an extravasation.

Impedance Gate. The impedance gate is used in the Run State. It is an impedance envelope around the epoch impedance average used as a baseline in the Run State. The purpose of the gate is to reduce the effect of noise. The gate envelope is less than the magnitude of an extravasation indicating signal. Epoch impedances outside the gate are relevant to the analysis to determine extravasation. In the embodiment disclosed the gate is ±1.33 ohms. Experience and application could vary the magnitude of the gate.

Epoch Impedance Slope (Also: Impedance Slope.). An epoch impedance slope is a value for the rate of change in impedance over a plurality of consecutive epochs. It is used in the Run State only. The slope is based on a sliding window of epochs. In this embodiment, an algebraic best-fit line using the least squares method is established for a sliding window of seven epoch impedances. The value of that slope is keyed to the last epoch in the window.

High Slope. When in the Run State, if the epoch impedance slope is consistently high, that is a sign there is an extravasation. In this embodiment, a high slope is one that is greater than plus 0.5 (+0.5) ohms per second or less than minus 0.5 (−0.5) ohms per second. The plus threshold is for non-ionic media. The minus threshold is for ionic media. The High Slope Counter counts these slopes.

Low Slope. An epoch impedance slope that is not a high slope is a low slope. Thus any slope between minus five and plus five is a low slope. A low slope increments the Low Slope Counter.

Gate Threshold. In the Run State, a gate of +1.33 ohm is set around the baseline impedance provided by the Have Baseline and Arm States. In order to initiate a detection of extravasation, a predetermined number of consecutive epoch impedances outside the gate must be detected in the Run State.

In this embodiment, that threshold number is seven (7) consecutive epochs having impedance outside the +1.33 ohm gate. An epoch average within the gate at any point during the Run State resets the gate threshold counter and all slope counters thereby restarting the Run State calculation.

High Slope Threshold. Once the gate threshold of seven has been met, epoch impedance slopes are calculated and counted. A threshold of a predetermined number of consecutive epoch high slope values are required immediately after seven out of gate impedances in order to advance the process toward an indication of extravasation. This threshold is seven (7) consecutive high slopes where the injection rate is low; that is, 4.0 ccs per second or less and is four (4) consecutive high slopes where the injection rate is high; that is, greater than 4.1 ccs per second.

Low Slope Reset. A low slope value in the Run State resets the High Slope Counter if the low slope value occurs during the establishment of the High Slope threshold.

After the High Slope threshold is met, then only if the Low Slope Counter equals a predetermined threshold is the High Slope Counter reset.

End Slope Check. As a final check to assure the minimization of false-positives, there is a requirement that there be three successive high slope epochs at the point where ten cc has been injected. If the three successive high slope epochs are not detected, the slope counters are reset. However, in one embodiment, these three successive high slope epochs can be any three in a five epoch band that brackets the epoch at which ten cc has been injected. There is an End Slope Counter which is used to determine these three epochs. The End Slope Counter is reset each time a low slope is detected.

False-Positive Since the purpose of this technique is to detect an extravasation, the detection is deemed a positive result. Thus, the term false-positive refers to a false indication of extravasation.

False-Negative. A false-negative simply means a failure to detect an extravasation that exists.

Reset. Counters are used to count the number of times certain events occur. For example, each time an epoch impedance is outside the impedance gate a particular counter indicates such. Another example, is that each high slope value is counted by another counter. Before the system get to the Run State (which is the point where the counters that indicate extravasation become operative), other measurements are made by counters which provide an indication that it is appropriate to go into the Run State. All these counters, those prior to the Run State and those used during the Run State, may be reset under certain conditions. The term reset is used herein to refer to the condition when one or more counters are reset to zero. This may occur before the Run State occurs because of an indication that an appropriate baseline cannot be provided. More significantly, certain counters that are used to determine extravasation will be reset when epoch impedance values or slope values are measured to be less than certain thresholds. This reset function is important to assure that the number of false positives (false indication of extravasation) are kept to a minimum and thus necessary to achieve one of the major objects of this invention.

Abort. Under certain conditions such as where there is equipment failure, the entire system is shut down. For example, if the leads to the patch which pick-up the signal break, the procedure is stopped. The term abort is used to refer to this situation. It involves the use of standard equipment test procedures. In the abort situation, the procedure stops. This differs from reset, which involves restarting some calculation or some part of the procedure.

Counters Employed.

There are six counters employed as part of the process of this invention. Four of these counters are used only in the Run State, which is the state where extravasation may be determined. Two of these counters are used in preliminary states which occur prior to the start of injection into a patient. The following is a list of counters with an indication of their function for reference to aid in reading the detailed description.

Stability Counter—Counts Good Epochs.

A. An Initial State must count two consecutive good epochs to switch to the Check for Stability State. Therefore, this counter is reset by a rejected epoch.

B. In the Check for Stability State, the stability counter must count twenty (20) consecutive good epochs to switch to the Have Baseline State. This counter is reset by either a rejected epoch or a bad epoch.

C. The Have Baseline State holds the state as long as there is a count of 75 good epochs and less than eight (8) consecutive bad epochs. Therefore the Stability Counter is reset when the Instability Counter counts eight consecutive bad epochs.

D. In the Run State this counter is not used. Instability Counter—Counts Bad Epochs.

A. In Initial State—not used.

B. In Check For Stability State, a count of one resets the Stability Counter.

C. In Have Baseline State, a count of eight consecutive bad epochs resets the Stability Counter. The Instability Counter is reset by a good epoch.

Epochs Out Of Gate Counter.

A. Used only in Run State. Must count seven (7) consecutive out of gate epochs to initiate the High Slope Counter count of slope calculations.

B. Reset when an epoch impedance drops within the gate.

High Slope Counter.

A. Used only in Run State.

B. Counts high slopes that is, slopes greater than 0.5 ohms per second and less than 0.5 ohms per second.

C. Must count a predetermined number of consecutive high slopes before extravasation can be declared.

D. It is reset:

(i) if the Epochs Out of Gate Counter is reset, or (ii) a low slope is detected during the count of consecutive high slopes, or (iii) if the Low Slope Counter counts a predetermined consecutive number of low slopes.

Low Slope Counter.

A. Used only in Run State.

B. Counts low slopes.

C. A count of a predetermined number of consecutive low slopes resets the High Slope Counter.

D. Reset when High Slope Counter is reset.

End Slope Counter

A. Used only in Run State.

B. Counts high slopes.

C. Must have a count of three (3) consecutive high slopes for extravasation to be indicated.

D. Reset when High Slope Counter is reset.

DESCRIPTION OF THE PREFERRED EMBODIMENTS

The System.

Figure 2:
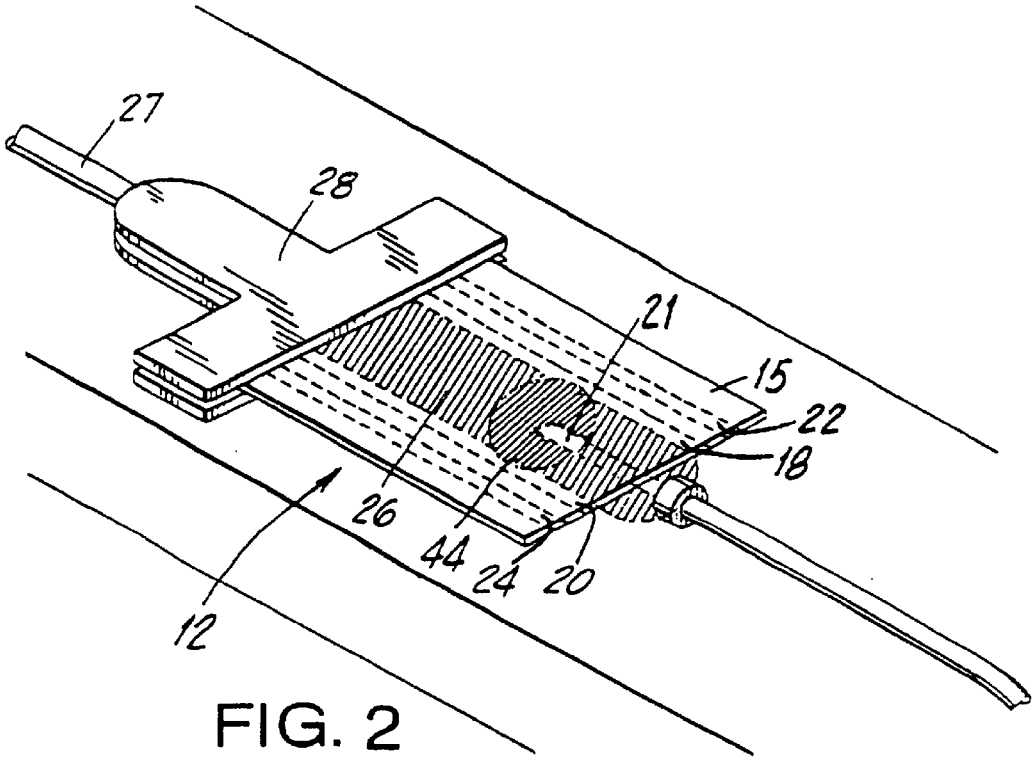
FIG. 2 is a more detailed diagrammatic view of the patch 12 of FIG. 1 that can be used in connection with the process of this invention. The patch is shown on a patient indicating, in idealized form, the relation between an extravasation 44 and the measuring zone 26.

As shown in FIGS. 1 and 2, a patch 12 applied to the skin of a patient includes a body 15 which has an adhesive backing that adheres the patch to the skin of the patient.

The patch contains surface electrodes 18, 20, 22 and 24. The inner electrodes 18 and 20 define a space 26 between them. The space 26 is shaped and dimensioned to permit a needle 21 to be placed thereunder. The clip 28 contains terminals which provide an energizing signal to the outer electrodes 22 and 24. The clip 28 also contains terminals which connect to the inner electrodes 18 and 20 and that will deliver a pick up signal that is sensed by the inner electrodes 18 and 20.

In one embodiment, each electrode has a length of about 7.6 cm and a width of about 0.5 cm. The inner electrodes 18 and 20 are spaced from one another by about 1.9 cm and the electrodes 22, 24 are spaced apart by about 3.8 cm. In that embodiment, the electrode patch 12 has a length of about 7.6 cm and a width of about five inches. When the syringe needle 21 is introduced into the patient's vasculature, a constant alternating current is applied to the two outer electrodes 22, 24.

In one embodiment, the current used is about 200 micro amperes at 20 kilohertz. The inner electrodes 18, 20 provide a measurement of voltage potential, the magnitude of which is a function of the impedance in the tissue under the zone 26.

The leads in the pick up electrodes 18, 20 are included in the conduit 27 and are connected to impedance monitoring and interpreting circuity 29 which provides an indication of the tissue impedance in the zone 26. This tissue impedance is affected by an extravasation such as the extravasation shown at 44. Ionic contrast media has a lower impedance than does tissue. Thus if ionic contrast media extravasation occurs, the effective impedance measured by the pick up electrodes 18, 20 will be less than the tissue impedance prior to extravasation. A non-ionic contrast media has a higher impedance than does the tissue and thus will cause an increase in impedance measurements during an extravasation.

When an injection is to be made, continuous calculations of tissue impedance are made both before and during the injection procedure. As explained in greater detail further on, an extravasation is deemed to have occurred if during the injection procedure the impedance change shows a fairly consistent slope of at least plus or minus five ohms per second. It is contemplated that in certain embodiments of the invention if a determination is made that an extravasation has occurred, there will be an automatic stop signal sent by conduit 40 to the injector 42 to cease the injection. Alternately, a visual or other type of warning signal can be provided so that the person administering the injection can take appropriate action.

Initial State.

The Initial State is in effect a bootstrap state. It is necessary to start the evaluation process running. The Initial State, like all of the states up to the Run State, is a process prior to the initiation of the injection into the patient. Once the equipment has been powered up and has been self tested by whatever routines are deemed to be appropriate so that the procedure can be started, resistance point readings are taken at the rate of twenty readings per 0.2 second duration epoch. The first epoch in the Initial State is established when at least eighty percent of the twenty consecutive points are within the predetermined impedance range of 40 ohms to 225 ohms. This 40 ohm to 225 ohm impedance range has been experimentally determined to be a range that will encompass almost every patient.

Once a first epoch has been so established, its impedance average is determined.

The next epoch is tested and determined to be an acceptable Initial State epoch if two criteria are met. The two criteria are: (1) eighty percent of its points are within a filter envelope and (2) it passes the base epsilon criteria. The filter envelope is set, in this embodiment, at plus or minus four ohms around the first epoch's impedance average. The filter is effective to eliminate spikes. The base epsilon criteria means that the epoch average of the second epoch must be within two ohms of the epoch average of the first epoch. If the second epoch does not meet these two criteria, then it is deemed to be a rejected epoch. A rejected epoch will cause a reset to the Initial State so that the testing of first and second epochs as described above will reoccur.

When two adjacent accepted epochs within the base epsilon criteria of one another have been determined, then the process is promoted to the next state which is the Check For Stability State.

Check For Stability State.

When the Initial State has been successfully processed, the processing routine moves to the Check For Stability State.

The Check For Stability State is successfully processed when twenty consecutive good epochs are detected. The Stability Counter provides this count.

A good epoch is different from an accepted epoch in that it must not only meet the criteria for an accepted epoch, but it must also meet the base epsilon criteria.

The first of the twenty epochs in the Check For Stability State also has to pass the base epsilon criteria and the immediately preceding epoch (which is the second of the two adjacent accepted epochs in the Initial State) is used to provide the average for the base epsilon ±2 ohm test for the first of the Check For Stability State epochs.

Since twenty consecutive good epochs are required to successfully go through the Check For Stability State, any accepted epoch that is not a good epoch is deemed a bad epoch and it resets the Stability Counter.

However, if at any time a rejected epoch (that is one containing fewer than eighty percent valid points out of the twenty points) is detected, then the entire processing is reset and the Initial State has to be successfully processed again.

Have Baseline State.

If the procedure has successfully processed through the Check For Stability State, it enters the Have Baseline State.

Although certain events can occur, as described below, which will cause the procedure to go back to the Reset State, the Have Baseline State is in part a waiting state. An epoch impedance baseline is determined for use in the Run State. The operator starts the Run State when an injection is to be started.

A sliding window of up to 75 epochs (covering fifteen seconds) is reviewed. The 75 epoch window is used to provide an average impedance based on valid points in the window. That average is the baseline employed during the Run State.

The valid points of all accepted epochs are included in the up to 75 epoch sliding window and the points in rejected epochs are ignored.

There is an Instability Counter which is incremented each time a rejected epoch and each time a bad epoch is detected. The rejected epoch fails the eighty percent valid point criteria and the bad epoch is an accepted epoch that fails the base epsilon criteria. When the Instability Counter indicates eight successive epochs that are not good epochs, this is an indication that the baseline has been lost and the whole system resets to the Initial State. Thus, every time a good epoch is detected (that is an accepted epoch which meets the base epsilon criteria), the Instability Counter is reset to zero. Since the good epoch is also an accepted epoch it is included in the sliding window.

The filter envelope is used to filter out spikes. It is equal to plus and minus four ohms about the average. It changes as the window average changes. It must be kept in mind that until 75 epochs do appear in the window, the points involved in the average will be from less than 75 epochs.

In addition to the filter envelope, there is a gate envelope which although not used in the Have Baseline State is calculated because it is used in connection with the subsequent Run State. This gate envelope is equal to the average epoch impedance in the window plus and minus 1.33 ohms in the embodiment involved.

The Have Baseline State does not terminate because of anything that occurs within the state (except for reset when the number of consecutive bad/rejected epochs exceeds eight) but continues until the next state is called for. The next state is called for only when the operator is ready to proceed.

Test Patch And Arm States.

If during the Baseline State, the operator is ready to proceed, the operator executes an arm command, usually by pressing an appropriate button. This arm command causes a test of the patch to be made to determine essentially that the leads to and from the patch have continuity. If this test fails, then the system aborts and the subsequent procedure is not undertaken because it is not available. However, if the test patch checks out, the system enters into the Arm State which is essentially like the Have Baseline State. An up to 75 epoch window average epoch impedance measurement is continued to provide the baseline to be employed during the succeeding Run State. In the Arm State, if an epoch average is outside the 40 ohm to 225 ohm range, the system resets to the Initial State.

When an injection is to be started and the Run command is provided from the operator, the next state, namely the Run State, is initiated.

Summary of Pre-Injection States.

Figure 3:
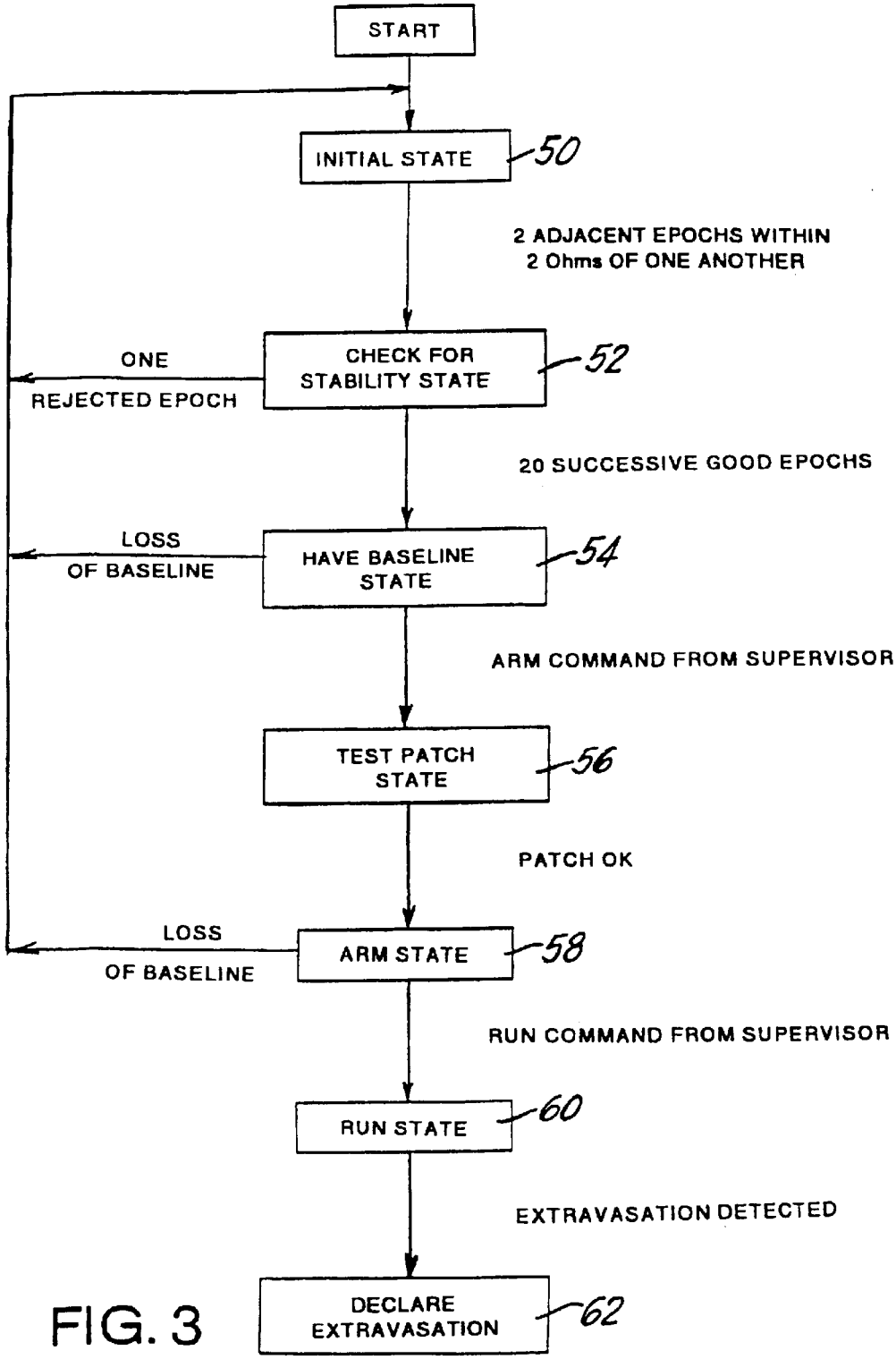
FIG. 3 is a state sequence chart showing the overall method of this invention and, in particular, the various states through which processing occurs. The states prior to the Run State occur prior to the start of injection and have as one object to establish a stable impedance baseline that is then used in the Run State as the base for comparison to determine whether or not there is an extravasation.

With the above disclosure in mind, FIG. 3 provides a useful summary thereof. As shown in FIG. 3, the Initial State 50 is exited when there are two adjacent epochs that meet the criteria that include the base epsilon criteria. The Check For Stability State 52 is exited to the next state when there are twenty successive good epochs. However, one rejected epoch sends the system back to the Initial State 50. The baseline provided by the Have Baseline State 54 is the baseline described above as the epoch impedance average over up to 75 epochs. However, if there is a loss of baseline, which means eight successive bad/rejected epochs, then the system goes back to the Initial State. The Have Baseline State is exited to the next state when an arm command is received from the supervisor.

When the Arm command is received, the patch is tested as indicated at Test State 56. If the patch test continuity shows that it is okay, then the system proceeds to the Arm State which essentially is a continuation of the Have Baseline State. Again, if there is a loss of baseline, the system goes back to the Initial State. Once the run command is received from the supervisor, the system goes into the Run State 60 and an extravasation is declared at step 62 if the Run State so detects. The description of the Run State is set forth in greater detail on the following pages.

It should be noted in connection with this system shown in FIG. 3 that hardware checks are regularly made. If there is a hardware failure including a failure of the test patch continuity, the whole system aborts and none of the processing in FIG. 3 is undertaken. In addition, the system can be reset to the Initial State if a stop command is received from the supervisor at any stage of the processing. Run State.

The Run State is the state within which extravasation, if there is one, is detected. The Run State starts at the beginning of the injection of the patient and is in response to the operator pressing a button that simultaneously initiates the Run State and the start of injection into the patient.

In the Run State, a consistent impedance change (slope) greater than a predetermined value is used to signal an extravasation. In the embodiment disclosed, a slope greater or less than 0.5 ohms per second must be consistently measured in order to indicate extravasation.

To minimize the risk of having a false signaling of extravasation, a gate is established around the baseline. The magnitude of that gate is based on experience. Only if the epoch impedance value is outside that gate is the slope criteria reviewed for the purpose of establishing an indication of extravasation. Indeed, in the preferred embodiment if even one epoch impedance falls within the gate, the Run State is reset and all the counters which count slope are reset to zero.

Thus, in this embodiment, there must be a consistent epoch impedance value outside of the gate and the epoch impedance slope must be consistently greater than a particular criteria. Both consistent high magnitude of impedance and consistent high rate of change of impedance are required to signal extravasation so as to assure a minimum risk of false signaling.

Figure 4:
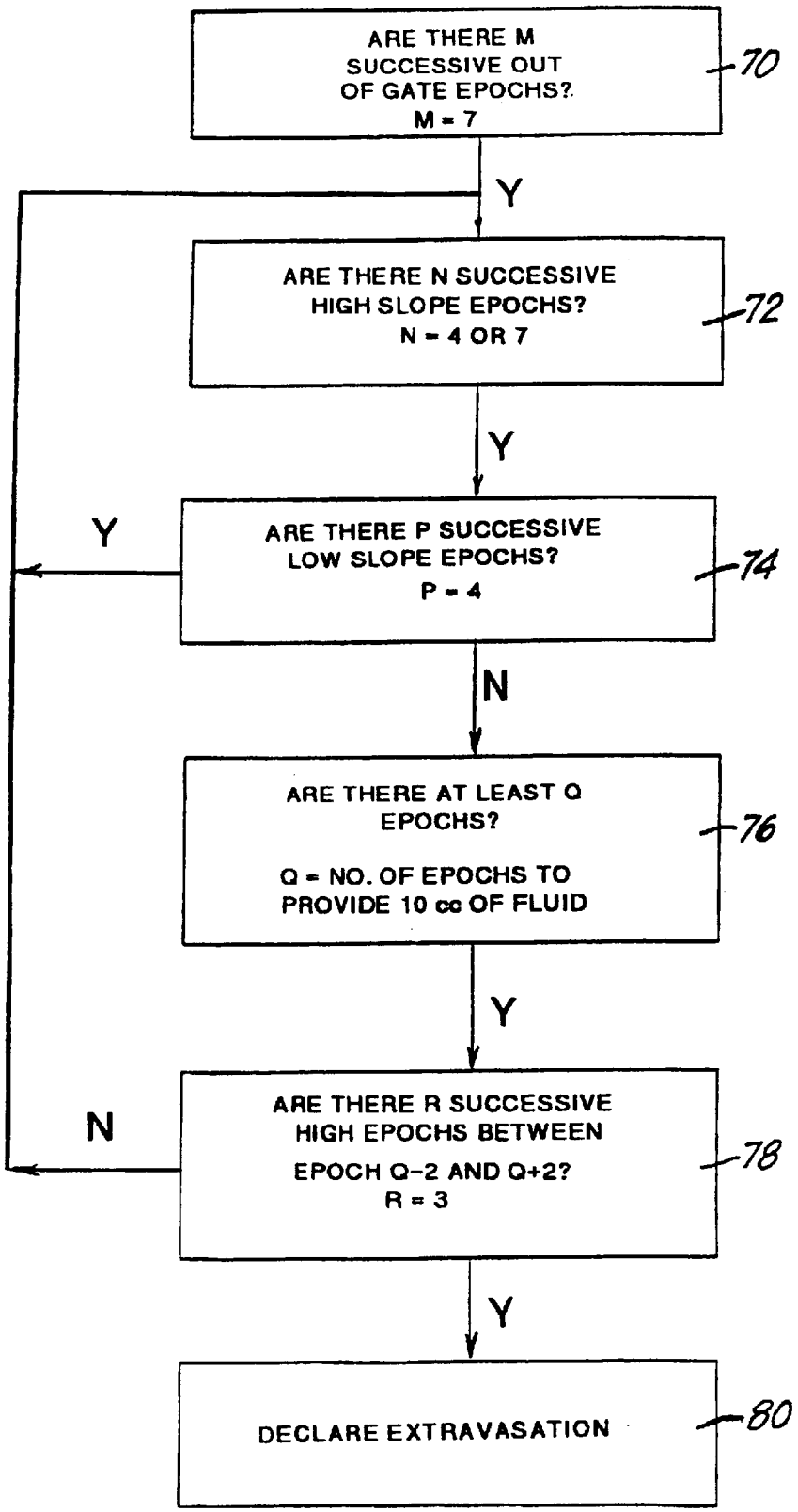
FIG. 4 is a high level partial flow chart of the Run State of this invention showing certain conditions that have to be detected prior to the determination that there is an extravasation.
Figure 5:
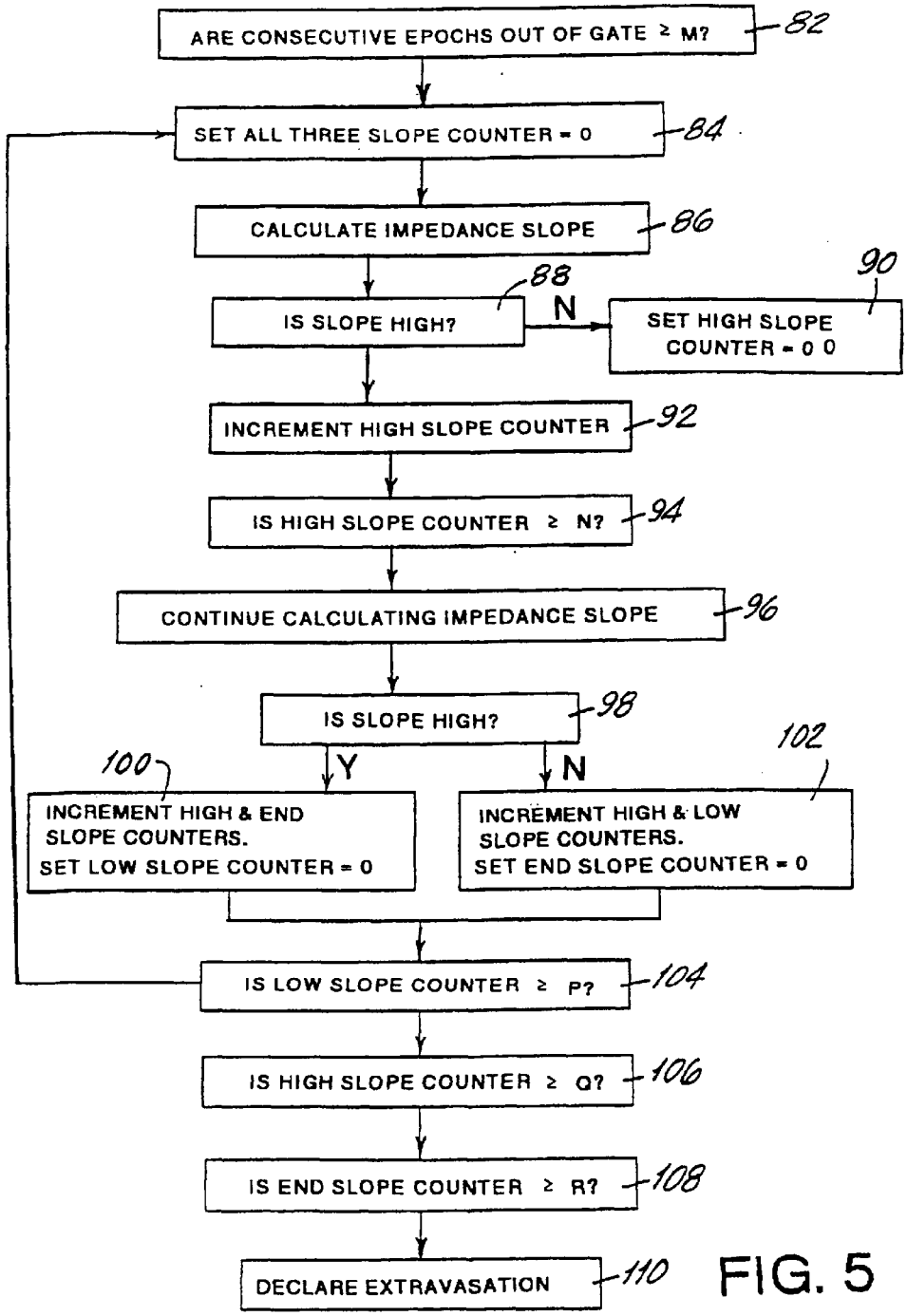
FIG. 5 is a more detailed partial flow chart showing processes that occur during the slope measurement stages of the Run State.

The following procedure explains in detail what is shown schematically in the logic flow diagrams of FIGS. 4 and 5.

Each epoch average is calculated and a determination is made if it is an accepted epoch. If it is a rejected epoch, it is ignored. If it is an accepted epoch then a determination is made as to whether or not it is within a gate of plus or minus 1.33 ohms about the baseline received from the previous state.

If an epoch average is outside of the gate, it increments an Epochs Out Counter. Seven consecutive outside of gate epoch averages are required before the system goes into the slope calculation. Thus each time the current epoch average is within the gate, the Epochs Out Counter is reset.

After the Epochs Out Counter provides a count of seven, the slope calculation is initiated. In the slope calculation, each individual epoch average that is outside the gate is stored in a slope sliding window. The slope sliding window covers seven epochs. The first slope calculation is based on the seven consecutive out of gate epochs that are a prerequisite to this slope calculation step.

A slope is calculated based on the slope of seven consecutive epochs. If that slope is greater or less than a particular threshold (Plus and minus 0.5 ohms per second in one embodiment), it is a high slope and a High Slope Counter is incremented.

The value of the slope is calculated from a best fit line using the least square method employing the epoch averages of each of seven consecutive epochs which are contained in the slope sliding window.

A Low Slope Counter is employed to count each slope that is within the ±0.5 ohm per second band. Its function is described below.

Once slope calculations start, they can be considered to operate in three phrases.

The first phase extends until the High Slope Counter indicates a predetermined number of consecutive high slope epochs. The predetermined number is a function of flow rate; seven at flow rates 4.0 cc/sec and less and four at flow rates 4.1 cc/sec and more. If even one epoch during the first phase is a low slope epoch, the High Slope Counter is reset. If the High Slope Counter counts to seven without being reset, the slope calculations enter into the second phase. It should be noted that the first high slope epoch calculation is made on the seventh of the seven successive out of gate epochs because the slope sliding window which encompasses that epoch and the preceding six epochs is operative.

In the second phase, the High Slope Counter is not reset by a low slope. During the second phase, a Low Slope Counter is also employed to count the number of low slopes that occur. If the number of consecutive low slopes equal a threshold then the High Slope Counter is reset and the first phase must be repeated. The low slope threshold is four.

Thus during the second phase if the number of consecutive low slope epochs exceeds a threshold, the slope calculation routine starts over. The low slope threshold does not put the system back to the start of the Run State.

What does put the system back to the start of the Run State is if any individual epoch impedance drops to within the gate. When that occurs, during the slope calculations, whether it is in the first, second or third phase of slope calculations, the Run State as such is reset and the Run State calculations start over including the requirement that there be the seven consecutive out of gate epochs.

In the second phase, assuming that the threshold number of consecutive low slope epochs does not occur, the High Slope Counter counts each epoch, whether it be a high slope or a low slope in order to provide a record of how many epochs have transpired. The technique requires that ten cc of fluid be injected before an extravasation can be declared. Thus there has to be at least Q epochs, representing when ten cc of fluid have been injected, as one of the criteria for an extravasation to be declared.

If the second phase of slope calculation has been completed, which means that there has been no reset of the High Slope counter and no reset of the Out Of Gate counter, the system proceeds to the third and final phase.

In the third phase, there is a requirement that there be a predetermined number of successive high slope epochs immediately before or immediately after the ten cc of fluid have been injected. Essentially this means that in the five epoch bracket between Q−2 epochs and Q+2 epochs there must be three successive high slope epochs.

If the third phase is also completed, then extravasation is declared and the system can be set up to either automatically stop the injection or to provide a signal so that the operator or doctor can make a determination as to what to do.

The same decision making requirements apply to all flow rates from the lowest to the highest. That is, for there to be an extravasation signal, each of the following situations must occur:

(a) There must be M successive out of gate epochs detected. In the embodiment, this number M is seven at all flow rates. The seven successive out of gate epochs must occur before the system starts to look at the slope counters.

(b) There must then be N successive high slope epochs. That number is a function of injection flow rate.

(c) A certain number P of successive low slope epochs must not occur.

(d) At least Q epochs must elapse from the start of the Run State before extravasation has been declared. The number of epochs Q is the number that assures that at least a certain minimum of fluid has been injected into the patient. In the embodiment involved, that minimum is ten cc of fluid. This means that Q is equal to fifty epochs at one cc per second and only ten epochs at five cc per second.

(e) At epoch Q, there must be R successive high slope epochs. In the embodiment disclosed, R is equal to three at all flow rates.

With the above description of the Run State in mind, FIG. 4 provides a useful logic chart or flow chart description of the main features of the Run State. As shown therein, the first step 70 is to determine that there are M successive out of gate epochs. If there are, then at step 72, N successive high slope epochs have to be detected. If they are, then one proceeds to the phase of accumulating Q epochs, as shown at step 76, to come to the point where ten cc of fluid have been injected into the patient. However, if during that step 76, a predetermined number P of successive low slope epochs occur as indicated at step 74, the process is set back to step 72.

As indicated earlier, the value of N is an inverse function of flow rate.

Once Q epochs have passed, extravasation will be declared as indicated at step 80 if R successive high slope epochs are indicated by the End Slope Epoch Counter in the five epochs that bracket the epoch Q. If those three successive high slope epochs are not found, the process resets to the step 72.

FIG. 5 provides a more detailed flow chart of the phases of the Run State wherein the epoch slopes are calculated and employed for the determination of extravasation.

As shown therein, the initial step 82 involves the requirement that there be the M consecutive epochs out of the gate in order to initiate the slope calculations. M equals seven in this embodiment. When there are seven consecutive out of gate epochs, then as indicated at step 84, all three slope counters are set to zero.

The system then proceeds to calculate each epoch slope as indicated at step 86. A determination is made (step 88) as to whether or not each epoch slope is high or low. If it is low (that is, not high) then at step 90 the High Slope Counter is set to zero. If the epoch slope is high, then step 92 increments the Slope Counter. Step 94 then determines if the High Slope Counter equals N; which in this embodiment is four or seven depending on flow rate. The next step, step 96, is to continue to calculate each epoch slope and determine whether at step 98 the slope is high or low. It should be noted that because of the step 90, for the High Slope Counter to equal N at step 94, there must be N consecutive high slopes. When step 98 identifies a high slope, the High Slope Counter and End Slope Counter are both incremented and the Low Slope Counter is set to zero (step 100). However if step 98 identifies a low slope, the High Slope Counter and the Low Slope Counter are both incremented and the End Slope Counter is set to zero (step 102).

The next step 104 is to determine if the Low Slope counter has a count equal to or greater than P; which in this embodiment has a value of four. Because at step 100 the Low Slope Counter resets in response to a high slope at step 98, the Low Slope Counter will equal P only if there are P successive low slopes. If there are P successive low slopes at step 104 then, as indicated, all three slope counters are set to zero and the slope calculations are started from the beginning.

However, if the Low Slope Counter never equals P, step 106 determines if the High Slope Counter is equal to Q. Q is the number of epochs to establish that the predetermined minimum injection fluid of ten cc has been completed. The value of Q reflects the fact that there is fluid injection during the M epochs at step 82.

When the High Slope Counter equals Q, then step 108 determines whether or not the End Slope Counter has a count of R, which in this embodiment, is three.

As described earlier, in one embodiment there is an additional routine wherein if the End Slope Counter does not read "3", then two additional epochs are processed to see if the reading of "3" is obtained, before the decision to reset or declare extravasation is made.

Certain Variations.

Although this invention has been described in connection with a particular embodiment, it would be obvious to one skilled in the art that various modifications can be made and would be made in connection with adapting to particular environments or if a different trade-off of false-positives and false-negatives were desired.

For example, there are a number of numerical parameters which could be adjusted to provide what a user might consider a more desirable or optimum arrangement. Such items as the size of the sliding window, the number of ccs in each injection before extravasation can be signaled and the band defined by the gate could be adjusted to provide different trade-offs of low false-positive and greater specificity. The inventive concepts are best defined in the claims and not in the particular value of the decision making parameters.

With reference to FIG. 4, the number of successive high slopes required at stage 72 might be increased beyond seven for low flow rates such as the flow rates between 0.25 and 1.5. As another example, the number of successive low slopes required for reset of the slope calculation at stage 74 might well be increased to a number greater than four at very low flow rates. Furthermore, it should be recognized that the criteria that P equals four at step 74 means that in effect this step has no meaningful impact at the higher flow rates and in particular flow rates greater than 3.1 cc per second.

One area that might be considered for variation in the above disclosure is that at very low flow rates (those well under one cc per second) the size of the slope sliding window which is used to make a slope calculation might be increased to greater than seven. This is a detail and adaptation that one skilled in the art would make depending upon the refinements desired and the trade-offs looked for.

Although the filter and gate envelopes are set in the Run State at values based on the baseline going into the Run State, in one embodiment an adjustment is made in the filter and gate envelopes at the end of 45 seconds to reflect whatever change there may have been in the epoch impedance average at that point.

What is claimed is:

1. The method of detecting extravasation that may occur when a needle is inserted into a patient for the purpose of delivering fluid into the patient's vascular system comprising the steps of:

prior to the delivery of fluid, establishing an impedance baseline for patient tissue impedance near the tip of the needle;

determining an impedance slope value based on deviations from said baseline for each of a plurality of time based epochs during the delivery of fluid, and signaling extravasation when said slope values are outside a first predetermined threshold with a consistency that meets a predetermined consistency criterion.

2. The method of claim 1 wherein:

said predetermined consistency criterion includes the combination of (a) a first predetermined number of out of threshold slopes, and (b) a second predetermined number of consecutive out of threshold slopes subsequent to the infusion of a predetermined volume of said fluid.

3. The method of claim 2 wherein said first predetermined number is of consecutive out of threshold slopes.

4. The method of claim 2 wherein said first predetermined number is inversely proportional to the rate at which fluid is delivered.

5. The method of claim 2 wherein said first predetermined number is greater than said second predetermined number.

6. The method of claim 2 wherein said step of determining a slope value comprises determining a best fit slope value over a predetermined number of epochs adjacent to the epoch for which said slope value is determined.

7. The method of claim 2 wherein said second predetermined number of out of threshold slopes commences after said first predetermined number of out of threshold slopes is determined.

8. The method of claim 2 wherein:

a sliding window of a plurality of epochs is employed to provide a base for the slope value determination, each slope value determination being based on a set of epochs that include epochs on which the preceding slope value determination was made.

9. The method of claim 1 wherein said step of determining a slope value comprises determining a best fit slope value over a predetermined number of epochs adjacent to the epoch for which said slope value is determined.

10. The method of claim 1 wherein:

a sliding window of a plurality of epochs is employed to provide a base for the slope value determination, each slope value determination being based on a set of epochs that include epochs on which the preceding slope value determination was made.

11. The method of claim 1 further comprising the steps of:

establishing said impedance baseline based on a first sliding window of epochs to provide an epoch impedance baseline, establishing a noise exclusion gate around said epoch impedance baseline, and during the delivery of fluid, providing a count of the number of consecutive epoch impedance averages which lie outside said gate, said step of signaling extravasation further requiring that said count of consecutive epoch impedance averages outside said gate exceeds a first value.

12. The method of claim 11 further comprising the steps of:

prior to said step of establishing an epoch impedance baseline, determining that there are a predetermined number of successive epochs each of which have an impedance average within a predetermined window.

13. The method of detecting extravasation that may occur when a needle is inserted into a patient for the purpose of introducing fluid into the patient's vascular system comprising the steps of:

prior to the delivery of fluid, establishing an epoch impedance baseline for patient tissue impedance near the tip of the needle based on a first sliding window of epochs, establishing a noise exclusion gate around said epoch impedance baseline, during the delivery of fluid, counting the number of consecutive impedance averages outside of said gate to provide a first count, establishing a second sliding window of epochs, determining an impedance slope for epoch impedance values over each of said second sliding windows of epochs, counting the number of consecutive ones of said impedance slopes having a value outside of a predetermined range to provide a second count, counting the total number of said impedance slopes having a value outside of said predetermined range to provide a third count, signaling extravasation when (a) said first count is greater than a first predetermined number, (b) said second count is greater than a second predetermined number, and (c) said third count is greater than a third predetermined number.

14. The method of claim 13 further comprising the steps of:

counting the number of consecutive ones of said impedance slopes adjacent to said third predetermined count having a value outside of said predetermined range to provide a fourth count, and wherein said step of signaling extravasation further requires that said fourth count be greater than a fourth predetermined number.

15. The method of claim 14 further comprising the steps of:

counting the number of consecutive ones of said impedance slopes having a value inside of said predetermined range, and resetting to said steps of counting to provide said first count.

16. The method of claim 14 wherein said first predetermined number is a count of consecutive averages outside said noise exclusion gate and wherein said first count is reset to zero when an epoch average falls within said noise exclusion gate.

17. The method of claim 13 further comprising the steps of:

counting the number of consecutive ones of said impedance slopes having a value inside of said predetermined range, and resetting to said steps of counting to provide said first count.

18. The method of claim 17 wherein said first predetermined number is a count of consecutive averages outside said noise exclusion gate and wherein said first count is reset to zero when an epoch average falls within said noise exclusion gate.

19. The method of claim 13 wherein said second and third predetermined numbers are inversely proportional to the rate at which fluid is delivered.

20. The method of claim 19 wherein said third predetermined number is greater than said second predetermined number.

21. The method of claim 13 wherein said second sliding windows include epochs that contribute to said first count.

22. The method of claim 13 wherein said first predetermined number is a count of consecutive averages outside said noise exclusion gate and wherein said first count is reset to zero when an epoch average falls within said noise exclusion gate.

*23. A non-invasive method of detecting extravasation when fluid is delivered into a patient's vascular system, comprising:*

*a) providing first and second electrodes; the electrodes being separated from each other to encompass the vicinity around an end of a channel inserted in the patient's vascular system for delivering fluid into the vascular system;*

*b) the first and second electrodes defining a measuring zone; the measuring zone being sized to detect extravasation in the measuring zone;*

*c) providing third and fourth electrodes to induce a signal between the first and second electrodes; said signal being a function of tissue impedance in the measuring zone; and*

*d) ascertaining if an extravasation has occurred by measuring changes in impedance within the measuring zone.*

*24. The method of claim 23, further comprising the step of energizing the third and fourth electrodes to induce the signal between the first and second electrodes.*

*25. The method of claim 24, further comprising the step of positioning a hydrogel material between the patient's skin and the electrodes.*

*26. The method of claim 23, further comprising the step of energizing the third and fourth electrodes with a current in the micro ampere range at a frequency of about 20 kilo-hertz.*

*27. The method of claim 23, further comprising the step of applying a hydrogel material on the electrodes.*

*28. The method of claim 23, further comprising the step of affixing the electrodes to the patient's skin.*

*29. The method of claim 23, further comprising the step of positioning the first and second electrodes between the third and fourth electrodes.*

*30. The method of claim 23, further comprising the step of deploying the first, second, third and fourth electrodes along a base, said base adapted to be affixed to the skin of a patient.*

*31. The method of claim 23, further comprising the step of providing, for each of the electrodes, a coupling region adapted for connection to a clip having electrical contacts.*

*32. A non-invasive method of detecting extravasation when fluid is delivered into a patient's vascular system, comprising:*

*a) providing first and second electrodes and third and fourth electrodes, said first and second electrodes being spaced from one another on either side of a center line, said first and second electrodes defining a measuring zone, said measuring zone being shaped and dimensioned to encompass within said zone an end of a channel inserted in a patient's vascular system for delivering fluid into the vascular system, said zone being sized to detect extravasation in the measuring zone and long enough to facilitate placement of the end of the channel within the measurement zone; each of said third and fourth electrodes being outward, relative to said center line,*

*b) energizing said third and fourth electrodes to provide a field which induces a signal in said first and second electrodes that is a function of tissue impedance in said measuring zone, and*

*c) ascertaining if an extravasation has occurred by measuring changes in impedance within the measuring zone.*

*33. The method of claim 32, further comprising the step of energizing the third and fourth electrodes to induce the signal between the first and second electrodes.*

*34. The method of claim 33, further comprising the step of positioning a hdyrogel material between the patient's skin and the electrodes.*

*35. The method of claim 32, further comprising the step of energizing the third and fourth electrodes with a current in the micro ampere range at a frequency of about 1 kilo-hertz to 20 kilo-hertz.*

*36. The method of claim 32, further comprising the step of applying a hydrogel material on the electrodes.*

*37. The method of claim 32, further comprising the step of affixing the electrodes to the patient's skin.*

*38. The method of claims 32, further comprising the step of positioning the first and second electrodes between the third and fourth electrodes.*

*39. The method of claims 32, further comprising the step of deploying the first, second, third and fourth electrodes along a base, said base adapted to be affixed to the skin of a patient.*

*40. The method of claims 32, further comprising the step of providing, for each of the electrodes, a coupling region adapted for connection to a clip having electrical contacts.*

*41. A non-invasive method of detecting extravasation when fluid is delivered into a patient's vascular system, comprising:*

*a) providing first and second electrodes; the electrodes being separated from each other to encompass the vicinity around an end of a channel inserted in the patient's vascular system for delivering fluid into the vascular system;*

*b) the first and second electrodes defining a measuring zone; the measuring zone being sized to detect extravasation in the measuring zone;*

*c) providing third and fourth electrodes to induce a signal between the first and second electrodes; said signal being a function of tissue impedance in the measuring zone;*

*d) ascertaining if an extravasation has occurred by measuring changes in impedance within the measuring zone; and*

*e) wherein the first, second, third and fourth electrodes are substantially the same length.*

*42. A non-invasive method of detecting extravasation when fluid is delivered into a patient's vascular system, comprising:*

*providing first and second electrodes; the electrodes being separated from each other to encompass the vicinity around an end of a channel inserted in the patient's vascular system for delivering fluid into the vascular system;*

*a) the first and second electrodes defining a measuring zone; the measuring zone being sized to detect extravasation in the measuring zone;*

*b) providing third and fourth electrodes to induce a signal between the first and second electrodes; said signal being a function of tissue impedance in the measuring zone;*

*c) ascertaining if an extravasation has occurred by measuring changes in impedance within the measuring zone; and*

*d) wherein the first, second, third and fourth electrodes are about 3 inches in length and about $3/16^{th}$ of an inch wide.*

*43. A non-invasive method of detecting extravasation when fluid is delivered into a patient's vascular system, comprising:*

*a) providing first and second electrodes; the electrodes being separated from each other to encompass the vicinity around an end of a channel inserted in the patient's vascular system for delivering fluid into the vascular system;*

*b) the first and second electrodes defining a measuring zone; the measuring zone being sized to detect extravasation in the measuring zone;*

*c) providing third and fourth electrodes to induce a signal between the first and second electrodes; said signal being a function of tissue impedance in the measuring zone;*

*d) ascertaining if an extravasation has occurred by measuring changes in impedance within the measuring zone; and*

*e) wherein the first, second, third and fourth electrodes are silver/silver chloride strips.*

*44. A non-invasive method of detecting extravasation when fluid is delivered into a patient's vascular system, comprising:*

*a) providing first and second electrodes; the electrodes being separated from each other to encompass the vicinity around an end of a channel inserted in the patient's vascular system for delivering fluid into the vascular system;*

*b) the first and second electrodes defining a measuring zone; the measuring zone being sized to detect extravasation in the measuring zone;*

*c) providing third and fourth electrodes to induce a signal between the first and second electrodes; said signal being a function of tissue impedance in the measuring zone;*

*d) ascertaining if an extravasation has occurred by measuring changes in impedance within the measuring zone; and*

*e) wherein the first and second electrodes are parallel relative to each other.*

*45. A non-invasive method of detecting extravasation when fluid is delivered into a patient's vascular system, comprising:*

*a) providing first and second electrodes; the electrodes being separated from each other to encompass the vicinity around an end of a channel inserted in the patient's vascular system for delivering fluid into the vascular system;*

*b) the first and second electrodes defining a measuring zone; the measuring zone being sized to detect extravasation in the measuring zone;*

*c) providing third and fourth electrodes to induce a signal between the first and second electrodes; said signal being a function of tissue impedance in the measuring zone;*

*d) ascertaining if an extravasation has occurred by measuring changes in impedance within the measuring zone; and*

*e) wherein the fourth and fifth electrodes are parallel to each other.*

* * * * *

UNITED STATES PATENT AND TRADEMARK OFFICE

CERTIFICATE OF CORRECTION

PATENT NO. : RE 38,879 E
APPLICATION NO. : 09/948277
DATED : November 15, 2005
INVENTOR(S) : Goodman et al.

It is certified that error appears in the above-identified patent and that said Letters Patent is hereby corrected as shown below:

Title page,
Item 56, References Cited, U.S. PATENT DOCUMENTS, "4,534,756" should read --4,535,756--.

Column 8,
Line 31, sentence beginning with "Once" should be a new paragraph.

Column 10,
Line 45, sentence beginning with "Run" should be a new paragraph.

Column 16,
Line 40, "encompass the" should read --encompass a--.

Column 17,
Line 62, "encompass the" should read --encompass a--.

Column 18,
Line 14, 35, 55, "encompass the" should read --encompass a--.

Column 19,
Line 10, "encompass the" should read --encompass a--.

Column 20,
Line 11, "fourth and fifth electrodes" should read --third a fourth electrodes--.

Signed and Sealed this

Ninth Day of January, 2007

JON W. DUDAS
*Director of the United States Patent and Trademark Office*